United States Patent [19]

Wyvratt, Jr.

[11] Patent Number: 4,622,313
[45] Date of Patent: Nov. 11, 1986

[54] O-SULFATE DERIVATIVES OF AVERMECTINS AND MILBEMYCINS HAVING IMPROVED WATER SOLUBILITY

[75] Inventor: Matthew J. Wyvratt, Jr., Mountainside, N.J.

[73] Assignee: Merck & Co., Inc., Rahway, N.J.

[21] Appl. No.: 761,247

[22] Filed: Aug. 1, 1985

[51] Int. Cl.$^4$ .................. A61K 31/70; A61K 31/365; C07H 17/08; C07D 493/22
[52] U.S. Cl. ........................................ 514/30; 536/71; 514/450; 549/264
[58] Field of Search .................. 536/7.1; 549/264; 514/30, 450

[56] References Cited

U.S. PATENT DOCUMENTS

| | | | |
|---|---|---|---|
| 3,950,360 | 4/1976 | Aoki et al. | 260/343.3 R |
| 4,171,314 | 10/1979 | Chabala et al. | 260/343.41 |
| 4,173,571 | 11/1979 | Chabala et al. | 260/343.41 |
| 4,199,569 | 4/1980 | Chabala et al. | 536/7.1 |
| 4,206,205 | 6/1980 | Mrozik et al. | 514/30 |
| 4,310,519 | 1/1982 | Albers-Schonberg et al. | 514/30 |
| 4,469,682 | 9/1984 | Mrozik | 549/264 |
| 4,470,976 | 9/1984 | Miner et al. | 536/4.1 |

OTHER PUBLICATIONS

Nishino et al., *Biochemistry*, 18 4340–4347 (1979).
Koster et al., *JACS* 105 3743–3745 (1983).
Galardy et al., *Biochem. J.*, 226 447–454 (1985).

*Primary Examiner*—Johnnie R. Brown
*Assistant Examiner*—Elli Peselev
*Attorney, Agent, or Firm*—David L. Rose; Salvatore C. Mitri; Michael C. Sudol, Jr.

[57] ABSTRACT

There are disclosed novel O-sulfate derivatives of avermectin and milbemycin. The avermectin and milbemycin O-sulfate derivatives have improved water solubility compared to the parent avermectin and milbemycin compounds and have utility as anti-parasitic agents and as potent insecticides against agricultural pests.

6 Claims, No Drawings

O-SULFATE DERIVATIVES OF AVERMECTINS AND MILBEMYCINS HAVING IMPROVED WATER SOLUBILITY

BACKGROUND OF THE INVENTION

The term avermectin (referrred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted at the 13-position with a 4'-($\alpha$-L-oleandrosyl)-$\alpha$-L-oleandrose group. The avermectin compounds and the instant derivatives thereof have a high degree of anthelmintic and anti-parasitic activity.

The avermectin series of compounds isolated from the fermentation broth have the following structure:

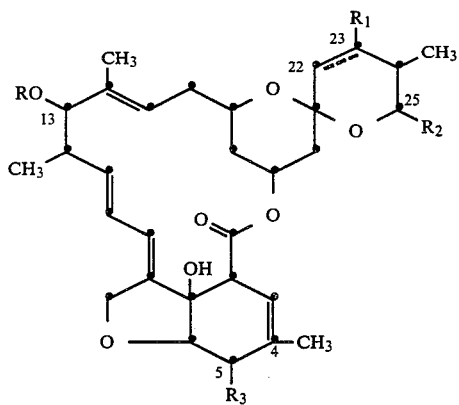

wherein R is the 4'-($\alpha$-L-oleandrosyl)-$\alpha$-L-oleardrose group of the structure:

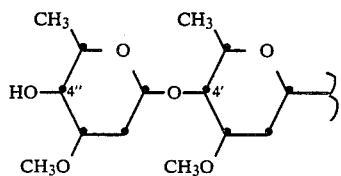

and wherein the broken line indicates a single or a double bond; $R_1$ is hydroxy and is present only when said broken line indicates a single bond;

$R_2$ is iso-propyl or sec-butyl; and $R_3$ is methoxy or hydroxy.

There are eight different major avermectin natural product compounds and they are given the designations A1a, A1b, A2a, A2b, B1a, B1b, B2a and B2b based upon the structure of the individual compounds.

In structural formula Ia above, the individual avermectin compounds are as set forth below wherein the R group is 4'-($\alpha$-L-oleandrosyl)-$\alpha$-L-oleandrose:

|     | $R_1$       | $R_2$      | $R_3$   |
|-----|-------------|------------|---------|
| A1a | Double Bond | sec-butyl  | —OCH$_3$ |
| A1b | Double Bond | iso-propyl | —OCH$_3$ |
| A2a | —OH         | sec-butyl  | —OCH$_3$ |
| A2B | —OH         | iso-propyl | —OCH$_3$ |
| B1a | Double Bond | sec-butyl  | —OH     |
| B1b | Double Bond | iso-propyl | —OH     |
| B2a | —OH         | sec-butyl  | —OH     |
| B2b | —OH         | iso-propyl | —OH     |

The avermectin compounds are generally isolated as mixtures of a and b components which differ only in the nature of the $R_2$ substituent. These minor structural differences have been found to have very little effect on the isolation procedures, chemical reactivity and biological activity of such compounds.

Milbemycin compounds are similar to the above avermectin compounds in that the 16-membered macrocyclic ring is present. However, such compounds have no substitution at the 13-position and have a methyl or ethyl group at the 25-position (i.e., the position of the $R_2$ group in the above structural formula I). To the extent that such milbemycin compounds have hydroxy groups or can be converted to compounds with hydroxy groups which can then be substituted with the instant O-sulfate groups, they are to be construed as being within the ambit of this invention. Such milbemycin compounds and the fermentation conditions used to prepare them are described in U.S. Pat. No. 3,950,360. In addition, 13-deoxyavermectin aglycones are prepared synthetically from the avermectin natural products and are disclosed in U.S. Pat. Nos. 4,171,134 and 4,173,571. Such compounds are very similar to the milbemycins differing from some of the milbemycins in having an isopropyl or sec butyl rather than a methyl or ethyl group at the 25-position.

U.S. Pat. No. 4,469,682 discloses phosphate esters of avermectin and milbemycin which are stated to have improved water solubility over the parent avermectin and milbemycin compounds and which are useful as anti-parasitic agents and insecticides.

The compounds of the present invention differ from those disclosed in U.S. Pat. No. 4,469,682 in that the instant compounds have an —SO$_3^\ominus$M$^\oplus$ group (defined hereinbelow) instead of the phosphate ester groups of the patent compounds. In addition, the instant compounds have a completely different heteroatom bonded to the averectin skeleton than those of disclosed in U.S. Pat. No. 4,469,682.

SUMMARY OF THE INVENTION

The instant invention is directed to O-sulfate derivatives of avermectins and milbemycins having improved water solubility and which are useful as anti-parasitic agents and insecticides.

DESCRIPTION OF THE INVENTION

The O-sulfate derivative avermectin and milbemycin compounds of the invention have the structural formula:

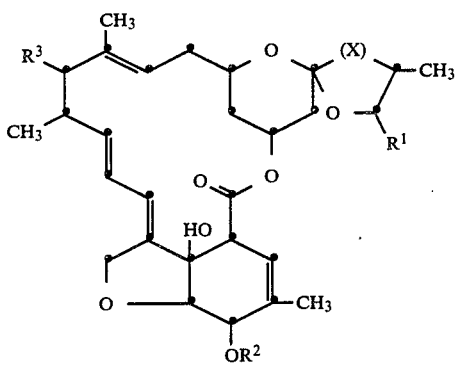

wherein:
X is

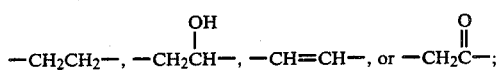

$R^1$ is methyl, ethyl, isopryl, or sec-butyl;

$R^2$ is hydrogen, methyl, or $-SO_3^\ominus M^\oplus$ wherein M is a member selected from the Group I elements (i.e., Li, Na, K, Rb, Cs, Fr), the Group II elements (i.e., Be, Mg, Ca, Sr, Ba, Ra) or an ammonium, dilower-alkyl ammonium, or pyridinium cation;

$R^3$ is hydrogen, hydroxy, $-OSO_3^\ominus M^\oplus$, α-L-oleandrosyloxy, 4'-(O)—$SO_3^\ominus M^\oplus$- (α-L-oleandrolsyloxy), 4'-(α-L-oleandrosyl)αL-oleandrosyloxy, 4"-(O)—$SO_3^\ominus M^\oplus$-4'- (α-L-oleandrosyl)-α -L-oleandrosyloxy wherein M is as defined above; provided that one of said $R^2$ or $R^3$ groups contains said $-SO_3^\ominus M^\oplus$ or $-OSO_3^\oplus M^\ominus$ substituents; and, physiologically acceptable salts thereof.

The term "loweralkyl" when used in the instant application represents those alkyl groups either straight or branched chain which have from 1-6 carbon atoms. Examples of such alkyl groups are methyl, ethyl, propyl, iso-propyl, butyl, sec-butyl, pentyl, and the like.

Preferred Formula III compounds of the instant invention, and their physiologically acceptable salts, are members of the group:

sodium 4"-O-sulfate-avermectin B1a/b;
sodium 4"-O-sulfate-22,23-dihydroavermectin B1a/b;
sodium 4',5-di-O-sulfate-22,23-dihydroavermectin B1a/b;
sodium 4",5-di-O-sulfate-avermectin B1a/b;
sodium 4'-O-sulfate-22,23-dihydroavermectin B1a/b monosaccharide;
sodium 4'-O-sulfate-avermectin B1a/b monosaccharide;
sodium 5-O-sulfate-13-deoxy-22,23-dihydroavermectin B1a/b aglycon;
sodium 4"-O-sulfate-avermectin A1a/b; and,
sodium 4"-O-sulfate-avermectin B2a/b.

The "b" compounds, those with a 25-isopropyl group, are very difficult to separate from the corresponding "a" compound with a 25-sec-butyl group and as such the compounds are generally isolated as mixtures of the two compounds. Thus, references in the instant application to "a" compounds such as B1a, A1a, and the like, are intended to define the pure compound as well as those which actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b, and the like.

PREPARATION OF STARTING MATERIALS

The starting materials for the compounds of this invention are the avermectin and milbemycin fermentation products defined above. Thus, it is apparent that additional reactions are required to prepare many of the starting materials for the instant compounds. Specifically, reactions are carried out at the 4', 4", 5, 13, 22, and 23-positions. It is generally preferred to prepare whatever substituents are required at these positions before carrying out the reaction to introduce the O-sulfate on the substrate. Such a procedure generally avoids undesirable side reactions. This technique is not required, however, and if desired other sequences may be used. In addition, during the sulfation reaction, it is sometimes necessary to protect hydroxy groups where reaction is not desired. With the appropriate positions protected, the reactions may be carried out without affecting the remainder of the molecule. Subsequently, the protecting group may be removed and the unprotected product isolated. The protecting group employed is ideally one which may be readily synthesized, will not be affected by the reaction conditions and may be readily removed without affecting any other functions of the molecule. In general, it is not required to protect the sterically hindered C7-hydroxy group.

It should be noted that the instant protected compounds are novel and have antiparasitic activity. They are included within the ambit of the instant invention. One preferred type of protecting group for the avermectin and milbemycin type of molecule is the tri-substituted silyl group, preferably the trialkyl silyl group. One especially preferred example, is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions. If it is desired to protect the 23-hydroxy group a 4", 5,23-tri(phenoxyacetyl) derivative can be prepared. Basic hydrolysis will leave the highy hindered 23-O-substituent but will hydrolize the 5- and 4"-O-phenoxy acetyl groups leaving them available for reaction. The 5-position can be selectively protected as described above with t-butyldimethylsilyl, and the 4" group can be reacted.

The silyl group can be removed after the other contemplated reactions are carried out. The silyl group or groups are removed by stirring the silyl compound in an acetic acid-water mixture. The reaction is complete in about 1 to 12 hours at from 0° to 50° C.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the 1-series of compounds. Thus in the "1" series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation; i.e., one that will selectively hydrogenate the least hindered from among a series of unsaturations. The preferred catalyst for such a selective hydrogenation procedure is one having the formula:

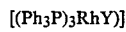

wherein

Ph is phenyl and Y is halogen. The reduction procedure is completely described in U.S. Pat. No. 4,199,569 to Chabala et al.

Additional reactions which can be carried out to prepare the compounds of this invention are the selective removal of one or both of the α-L-oleandrosyl moieties (described in U.S. Pat. No. 4,206,205 to Mrozik et al.) or the selective acylation of the susceptible hydroxy groups (described in U.S. Pat. No. 4,201,861 to Mrozik et al.).

The reaction conditions which are generally applicable to the preparation of both the monosaccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20°–40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which can be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the monosaccharide and the aglycone. The procedure for the preparation of the monosaccharide uses 1% acid by volume in isopropanol at from 20°–40° C., preferably room temperature, for from 6 to 24 hours. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

The compounds wherein $R^3$ is hydrogen are prepared from the avermectin starting materials as described hereinbelow. The reaction at the 13-position can generally be carried either before or after the other above described reactions.

The series of reactions at the 13-position commences with the removal of the α-L-oleandrosyl-α-L-oleandrose side chain as described above. The avermectin aglycone compounds are then halogenated with a suitably reactive benzenesulfonyl chloride or bromide in the presence of a base to produce the "13-deoxy-13-halo-avermectin-aglycone" compounds. The halogen is then removed in a reaction with a trialkyltinhydride to produce the "13-deoxyavermectin aglycone compounds." The aglycone compounds are prepared using procedures described above.

The procedures for the preparation of the 13-deoxy compounds are described in detail in U.S. Pat. Nos. 4,171,134 and 4,173,571 to Chabala et al.

The 23-hydroxy group is oxidized to the 23-keto group to form the compounds wherein $R_1$ is $=O$, using oxidizing agents such as pyridinium dichromate; oxalylchloride-dimethylsulfoxide; acetic anhydride-dimethylsulfoxide; chromic acid-dimethylpyrazole; chromic acid; trifluoromethylacetic anhydride-dimethylsulfoxide; chromic acid-acetic acid; and the like. Oxalylchloride-dimethylsulfoxide is the preferred oxidizing agent. Suitably protected compounds, as described below, are employed. The reaction is carried out at from dry-ice bath temperatures to room temperature, preferably from dry-ice bath temperatures to 0° C. and is complete in from 1–24 hours. The reaction can be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chromic acid-dimethylpyrazole reactions, methylene chloride is preferred. The compounds are isolated from the reaction mixture using procedures known to those skilled in the art.

The novel compounds of this invention have parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasties of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as two-spotted spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by administering about 0.001 to 10 mg of drug per kg of animal body weight, such total dose being given at one time or in divided doses over a relatively short period of time such as 1–5 days. With the preferred compounds of the invention, control of such parasties is obtained in animals by administering from about 0.025 to 1 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. An inert carrier is one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parastic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant proceses, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

DETAILED DESCRIPTION OF THE INVENTION

Preparation of the O-sulfate avermectin and milbemycin derivative compounds of the invention is illustrated in the following Reaction Scheme for 4''-(O)—SO$_3^\ominus$Na$^\oplus$-22,23-dihydroavermectin B.

REACTION SCHEME

Synthesis of 4''-(O)—SO$_3^\ominus$Na$^\oplus$—22,23-dihydroavermectin B

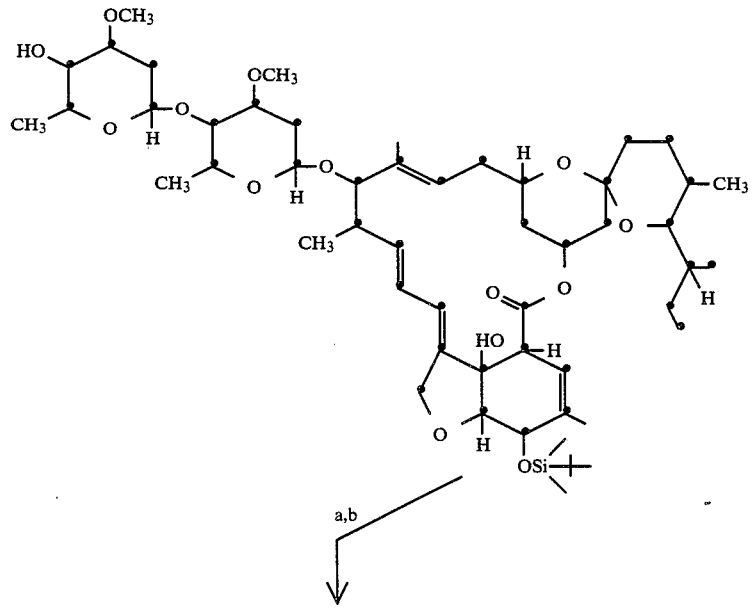

REACTION SCHEME

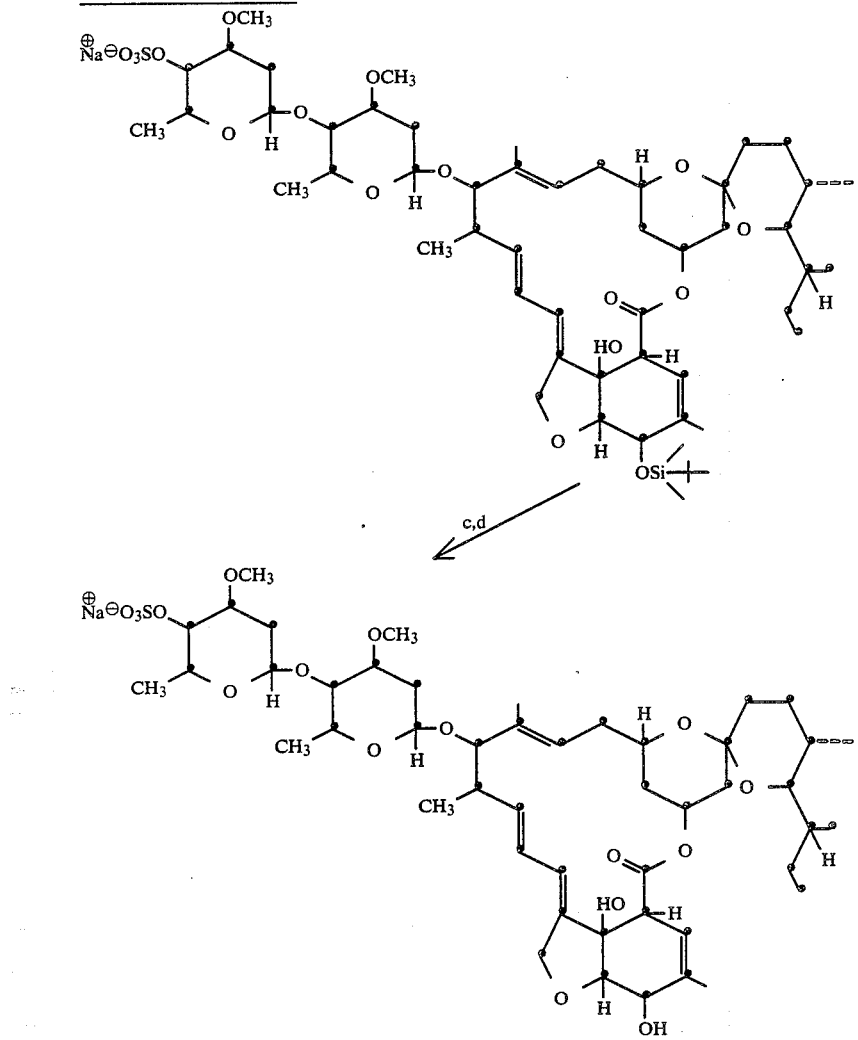

Conditions:

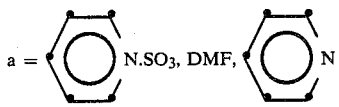

b = NaOH
c = 30:70 HOAc:H₂O
d = chromatography on HP-20

The protected avermectin derivative (one equivalent) is dissolved in dry N,N-dimethylformamide (DMF). Four equivalents of dry pyridine is added to this mixture followed by the slow addition of a solution of two equivalents of sulfur trioxidepyridine complex in DMF. The reaction is conveniently monitored by HPLC on a reverse phase column using a solvent system consisting of acetonitrile and a tetra-n-butylammonium phosphate buffer. If the reaction has not gone to completion at this point, additional quantities of pyridine and the sulfating reagent may be added until HPLC indicates that all or most of the starting avermectin derivative has been consumed.

The reaction mixture is then added to water and the pH of the resulting solution adjusted to near neutrality with an aqueous sodium hydroxide solution. The 5-silyl protecting group can then be removed in an acetic acid-water solvent system and the resulting product purified on HP-20 resin to give the desired sulfated avermectin derivative.

The other derivatives are prepared under similar conditions.

The following examples are provided in order to more fully describe the present invention and are not to be construed as limitative of the invention.

The substituted avermectin derivatives prepared in the following examples are generally isolated as solids. They are characterized analytically using techniques such as mass spectrometry, nuclear magnetic resonance, and the like. The compounds are not characterized by sharp melting points; however, the chromatographic and analytical methods employed indicate that the compounds are pure.

In the following examples, the various starting materials therefore are avermectin compounds or derivatives of avermectin compounds. The avermectin compounds and the preparation and isolation thereof from fermentation broths are described in U.S. Pat. No. 4,310,519. The selective 22,23-dihydro derivatives of avermectin compounds are described in U.S. Pat. No. 4,199,569. The aglycone and monosaccharide derivatives of avermectin compounds are described in U.S. Pat. No. 4,206,205.

EXAMPLE 1

Sodium 4"-O-Sulfate-5-O-(tert-butyldimethylsilyl)-22,23-dihydroavermectin $B_1$

To a solution of 5-O-(tert-butyldimethylsilyl)-22,23-dihydroavermectin $B_1$ (197 mg, 0.2 mmol) and pyridine (65 μl, 0.8 mmol) in 5 ml of dry N,N-dimethylformamide (DMF), a solution of sulfur trioxide-pyridine complex (64 mg) in 0.75 ml of DMF was added slowly over ten minutes under a nitrogen atmosphere. The reaction was conveniently monitored by HPLC on a reverse phase (RP-18) analytical column [Whatman ODS-3, 65–80% gradient, acetonitrile/0.005M tetra-n-butylammonium phosphate buffer (pH 7.0), 44° C.]. The reaction mixture was stirred for 3 hours and then diluted with 40 ml of water. The pH of the resulting solution was adjusted to 7.75 with 0.1N sodium hydroxide solution. The solution was then carefully concentrated under reduced pressure and the residue dried on a vacuum pump overnight. The residue was suspended in methanol and the resulting solid sodium sulfate removed by centrifugation. The methanolic solution was concentrated to give 200 mg of sodium 4"-O-sulfate-5-O-(tert-butyldimethylsilyl)-22,23-dihydroavermectin $B_1$, m.p. 188° (dec). The $^1$H NMR spectrum (CD$_3$OD) of the product showed a downfield shift of approximately 1 ppm for the 4"-hydrogen when compared with the 4"-hydrogen in 5-O-(tert-butyldimethylsilyl)-22,23-dihydroavermectin $B_1$. The product also exhibited additional spectroscopic data (UV, mass spectrum-FAB) consistent with its structure.

Microanalysis: Calc'd. for $C_{54}H_{87}O_{17}SSiNa\cdot0.5H_2O$: C, 58.94; H, 8.06; S, 2.91. Found: C, 58.79; H, 7.96; S, 2.89.

EXAMPLE 2

Sodium 4"-O-Sulfate-22,23-dihydroavermectin $B_1$

A solution of sodium 4"-O-sulfate-5-O-(tertbutyldimethylsilyl)-22,23-dihydroavermectin $B_1$ (120 mg) in 25 ml of an acetic acid-water mixture (30:70) was stirred at room temperature for 5.5 hours. The reaction mixture was then carefully concentrated and dried under reduced pressure overnight. HPLC analysis indicated the desired product plus <2% of 22,23-dihydroavermectin $B_1$ monosaccharide. The crude product was dissolved in 30 ml of water and the pH adjusted to neutrality. The solution was then chromatographed on a HP-20 column (40 ml of resin). The column was eluted with aqueous solvents in the following order: water (200 ml), 1:1 MeOH/H$_2$O (300 ml), and then 3:1 MeOH/H$_2$O. The fractions were analyzed by HPLC and the appropriate fractions combined and concentrated to give 77.5 mg of pure sodium 4"-O-sulfate-22,23-dihydroavermectin $B_1$. The product exhibited characteristic $^1$H NMR and mass spectroscopy (FAB) data.

Microanalysis: Calc'd. for $C_{48}H_{73}O_{17}SNa$: C, 59.00; H, 7.53; S, 3.28. Found: C, 58.86; H, 7.56; S, 3.28.

EXAMPLE 3

Sodium 4",5-di-O-Sulfate-22,23-dihydroavermectin $B_1$

To a solution of dried 22,23-dihydroavermectin $B_1$ (175 mg) and pyridine (97 μl) in 5 ml of dry DMF, a solution of sulfur trioxide-pyridine complex 95.6 mg, in 1 ml of DMF was slowly added over 20 minutes. The reaction mixture was stirred for an additional two hours prior to dilution with water (40 ml). The pH of this solution was then adjusted to 7.25 with 0.1N sodium hydroxide solution. The reaction mixture was carefully concentrated under vacuum (caution: foamy). The residue was suspended in methanol and the solid sodium sulfate removed by centrifugation. The methanolic fraction was concentrated to give 231 mg of crude product which was then chromatographed on a HP-20 column (50 ml of resin). The column was eluted with various aqueous-methanol mixtures (0% to 100% methanol). The fractions were analyzed by HPLC and the appropriate fractions combined and concentrated to give 211 mg (98%) of sodium 4",5-di-O-sulfate-22,23-dihydroavermectin $B_1$. The $^1$H NMR spectrum (CD$_3$OD) of the product showed a characteristic downfield shift for the 4"-hydrogen and the 5-hydrogen when compared with the spectrum for 22,23-dihydroavermectin $B_1$.

Microanalysis: Calc'd. for $C_{48}H_{72}O_{20}S_2Na_2$: C, 53.42; H, 6.73; S, 5.94. Found: C, 53.18; H, 6.69; S, 5.89.

EXAMPLE 4

Sodium 4"-O-Sulfate-5-O-(tert-butyldimethylsilyl)-avermectin $B_1$

To a solution of 5-O-(tert-butyldimethylsilyl)avermectin $B_1$ (197 mg) and pyridine (63 mg) in 5 ml of dry DMF under nitrogen, a solution of sulfur trioxide-pyridine complex (64 mg, 0.4 mmol) in 0.5 ml of DMF was slowly added via syringe over ten minutes. The reaction mixture was stirred for 2.5 hours and then diluted with 40 ml of H$_2$O. The pH of this solution was adjusted from 4.35 to 7.35 with 0.1N sodium hydroxide solution. The reaction mixture was then concentrated (in vacuo) and the residue dried overnight. The residue was partitioned in methanol and the insoluble sodium sulfate removed by centrifugation. The methanolic fraction was concentrated to afford 192 mg of product. Spectroscopic data ($^1$H NMR UV, mass spectrum-FAB) was consistent with the assigned structure.

EXAMPLE 5

Sodium 4"-O-Sulfate-avermectin $B_1$

A solution of sodium 4"-O-sulfate-5-O-(tert-butyldimethylsilyl)avermectin $B_1$ (172 mg) in 25 ml of an acetic acid-water mixture (30:70) was stirred at ambient temperature for 6.5 hours. The reaction mixture was concentrated and dried under vacuum overnight. The residue was dissolved in 30 ml of water and the pH of the solution adjusted to 7.0 with 0.1N NaOH. This solution was then chromatographed on a HP-20 column (40 ml of resin). The column was eluted with various methanol-water mixtures (0%, 30%, 50%, 75%, 100% methanol). The fractions were analyzed by HPLC [Whatman ODS-3 RP-18 column, 45–65% gradient, acetonitrile/0.005M tetra-n-butylammonium phosphate buffer (pH 7.0), 44° C.] and the appropriate fractions combined and concentrated to give 120 mg (78%) of pure sodium 4"-O-sulfate-avermectin $B_1$. The $^1H$ NMR spectrum ($CD_3OD$) exhibited the characteristic downfield shift for the 4"-hydrogen ($\delta 4.0$). The UV and mass spectral (FAB) data were also in agreement with the structure.

Microanalysis: Calc'd. for $C_{48}H_{71}O_{17}SNa \cdot 3H_2O$: C, 56.01; H, 7.54; S, 3.12. Found: C, 56.05; H, 7.22; S, 2.98.

EXAMPLE 6

Sodium 4",5-di-O-Sulfate-avermectin $B_1$

A solution of avermectin $B_1$ (175 mg) and pyridine (96 mg) in 5 ml of DMF can be slowly treated with a solution of sulfur trioxide-pyridine complex (96 mg) in 1 ml of DMF and the reaction permitted to stir under nitrogen until HPLC indicates the reaction has gone to completion. (If necessary, additional sulfating reagent can be added.) The reaction mixture can then be diluted with water (40 ml) and the pH adjusted to near neutrality with 0.1N NaOH. Careful concentration of the reaction mixture under vacuum can afford a solid residue which can then be suspended in methanol and the insoluble inorganic salts removed by centrifugation. The methanolic solution can be concentrated and the crude product chromatographed on HP-20 resin. Elution with various methanol-water mixtures will afford sodium 4",5-di-O-sulfate-avermectin $B_1$.

EXAMPLE 7

Sodium 4'-O-Sulfate-5-O-(tert-butyldimethylsilyl)-22,23-dihydroavermectin $B_1$ Monosaccharide To a solution of 5-O-(tert-butyldimethylsilyl)-22,23-dihydroavermectin $B_1$ monosaccharide (169 mg) and pyridine (63 mg) in 5 ml of dry DMF, a solution of sulfur trioxide-pyridine complex (64 mg) in 1 ml of dry DMF was slowly added under a nitrogen atmosphere. Reaction was monitored by HPLC and an additional 20 mg of sulfur trioxide-pyridine complex was required to complete the reaction. The reaction mixture was stirred for 2.5 hours and then diluted with water (40 ml). The pH of the solution was adjusted with 0.1N NaOH to 7.0 and then carefully concentrated under vacuum. The residue was suspended in methanol and the insoluble sodium sulfate removed by centrifugation. The methanolic solution was concentrated to give 195 mg of sodium 4'-O-sulfate-5-O-(tert-butyldimethyl)-22,23-dihydroavermectin $B_1$ monosaccharide. Mass spectral examination (FAB) revealed a molecular ion at 924 (M-Na). $^1H$ NMR indicated that the 4'-hydrogen had shifted downfield to $\delta 4.1$.

Microanalysis: Calc'd. for $C_{47}H_{75}O_{14}SSiNa \cdot H_2O$: C, 58.48; H, 8.04; S, 3.32. Found: C, 58.51; H, 7.97; S, 3.29.

EXAMPLE 8

Sodium 4'-O-sulfate-22,23-dihydroavermectin $B_1$ Monosaccharide

A solution of sodium 4'-O-sulfate-5-O-(tert-butyldimethylsilyl)-22,23-dihydroavermectin $B_1$ monosaccharide (169 mg) in 25 ml of an acetic acid-water mixture (30:70) was stirred at ambient temperature for 6 hours. The reaction mixture was concentrated and the residue dried overnight. The crude product was dissolved in 30 ml of water and the pH adjusted to 7.5 with 0.1N sodium hydroxide. This aqueous solution was then placed on a HP-20 (50 ml of resin) column. The column was then eluted with various methanol-water mixtures (0%, 30%, 50%, 75%, 100% methanol). The fractions were analyzed by HPLC (same conditions as in Example 5) and the appropriate fractions combined and concentrated to give 129 mg (87%) of sodium 4'-O-sulfate-22,23-dihydroavermectin $B_1$ monosaccharide. Mass spectral analysis (FAB) indicated a molecular ion at 809 (M-Na).

Microanalysis: Calc'd. for $C_{41}H_{61}O_{14}SNa$: C, 59.11; H, 7.38; S, 3.85. Found: C, 58.41; H, 7.29; S, 3.74.

EXAMPLE 9

Sodium 4'-O-sulfate-5-O-(tert-butyldimethylsilyl)-avermectin $B_1$ Monosaccharide To a solution of 5-O-(tert-butyldimethylsilyl)avermectin $B_1$ monosaccharide (168 mg) and pyridine (63 mg) in 5 ml of dry DMF, a solution of sulfur trioxide pyridine complex (64 mg) in 1 ml of DMF can be slowly added. The reaction mixture can then be stirred under nitrogen until HPLC indicates complete reaction. Additional reagent may be required to complete the reaction. The mixture can then be diluted with water (40 ml) and the pH of the resulting aqueous solution adjusted to 7.0 with dilute sodium hydroxide. The reaction mixture can then be carefully concentrated under vacuum and the remaining residue suspended in methanol. The insoluble inorganic salts can be removed by centrifugation. The methanolic solution can be concentrated to give sodium 4'-O-sulfate-5-O-(tert-butyldimethylsilyl)-avermectin $B_1$ monosaccharide.

EXAMPLE 10

Sodium 4'-O-sulfate-avermectin $B_1$ Monosaccharide

A solution of sodium 4"-O-sulfate-5-O-(tert-butyldimethylsilyl)avermectin $B_1$ monosaccharide (85 mg) in 15 ml of a 30:70 acetic acid-water mixture can be stirred for approximately 6 hours. The reaction mixture can be carefully concentrated and the residue dried overnight under vacuum. The crude product can then be dissolved in 20 ml of water and the pH adjusted to neutrality with 0.1N sodium hydroxide. This aqueous solution can then be added to a HP-20 column (30 ml of resin). The column can then be eluted with various methanol-water mixtures ranging from 0% to 100% methanol. The fractions can be analyzed by HPLC and the appropriate fractions combined and concentrated to give pure 4'-O-sulfate-avermectin $B_1$ monosaccharide.

EXAMPLE 11

Sodium 4"-O-sulfate-avermectin $A_1$

To a solution of 175 mg of avermectin $A_1$ and 95 mg of pyridine in 5 ml of dry pyridine under nitrogen, a solution of sulfur trioxide-DMF complex (95 mg) in 1 ml of DMF can be slowly added via a syringe. The reaction mixture can then be stirred until HPLC indicates complete reaction. The mixture can then be diluted with water (40 ml) and the pH of the resulting solution adjusted to 7.0 with dilute base (NaOH). The reaction mixture can then be concentrated and the solid residue suspended in methanol. The insoluble inorganic salts can be collected by means of centrifugation. The methanolic fraction can be concentrated and the residue dissolved in water and chromatographed on HP-20 resin (40 ml). Elution with methanol-water mixtures would yield pure sodium 4″-O-sulfate-avermectin A₁.

EXAMPLE 12

Sodium 4″-O-sulfate-5-O-(tert-butyldimethylsilyl)-avermectin B₂

To a solution of 5-O-(tert-butyldimethylsilyl)avermectin B₂ (200 mg) and pyridine (65 μl ) in 5 ml of dry DMF, a solution of sulfur trioxidepyridine complex (64 mg) in 1 ml of DMF can be slowly added. The reaction can be stirred at ambient temperature until HPLC indicates complete reaction. (Additional sulfating reagent can be added if necessary). The reaction mixture can then be diluted with water (40 ml) and the pH of the resulting solution adjusted to near neurality with 0.1N sodium hydroxide. The solution can then be carefully concentrated to dryness. The residue can be suspended in methanol and the inorganic salts separated by centrifugation. The methanolic solution can then be concentrated to give sodium 4″-O-sulfate-5-O-(tert-butyldimethylsilyl)avermectin B₂.

EXAMPLE 13

Sodium 4″-O-sulfate-avermectin B₂

A solution of sodium 4″-O-sulfate-5-O-(tert-butyldimethylsilyl)avermectin B₂ (120 mg) in 25 ml of a 30:70 acetic acid:water mixture can be stirred until complete deblocking has been effected. The reaction mixture can be concentrated and redissolved in water. The pH of this solution can be adjusted to 7.0 with 0.1N NaOH and the solution then added to a HP-20 column (40 ml). The column can then be eluted with various methanol-water mixtures (0%, 30%, 50%, 75%, 100% methanol). The fractions can be analyzed by HPLC and the appropriate fractions combined and concentrated to give sodium 4″-O-sulfate-avermectin B₂.

EXAMPLE 14

Sodium 5-O-(tert-butyldimethylsilyl)-13-O-sulfate-22,23-dihydroavermectin B₁ Aglycon To a solution of 65.5 mg of 5-O-(tert-butyldimethylsilyl)-22,23-dihydroavermectin B₁ aglycon and 30 μl of pyridine in 2.5 ml of dry DMF, a solution of sulfur trioxide-pyridine complex (30 mg) in 0.5 ml of DMF can be added slowly under nitrogen. The reaction mixture can then be stirred until HPLC indicates near complete reaction. The mixture can then be diluted with water (25 ml) and the pH adjusted to near neutrality with 0.1N sodium hydroxide. The reaction mixture can be concentrated under vacuum and the residue partially suspended in methanol. The inorganic salts can be removed by centrifugation and the methanolic portion concentrated to give the product.

EXAMPLE 15

Sodium 13-O-sulfate-22,23-dihydroavermectin B₁ Aglycon

A solution of sodium 5-O-(tert-butyldimethylsilyl)-13-O-sulfate-22,23-dihydroavermectin B₁ aglycon (60 mg) in 15 ml of an acetic acid-water mixture (30:70) can be stirred at room temperature for 6 hours. The reaction mixture can then be concentrated under vacuum and the resulting residue dissolved in 15 ml of water and the pH adjusted to 7.0 with 0.1N NaOH. The aqueous solution can then be added to a HP-20 column (30 ml of resin) and the column eluted with various methanol-water mixtures. The fractions can be analyzed by HPLC and the appropriate fractions concentrated to give pure sodium 13-O-sulfate-22,23-dihydroavermectin B₁ aglycon.

EXAMPLE 16

Sodium 5-O-sulfate-13-Deoxy-22,23-dihydroavermectin B₁ Aglycon

To a solution of 53.4 mg of 13-deoxy-22,23-dihydroavermectin B₁ aglycon [H. Mrozik, et al., Tetrahedron Lett., 24, 533 (1983)] and 30 μl of pyridine in 2.5 ml of dry DMF, a solution of sulfur trioxide-pyridine complex (30 mg) in 0.5 ml of DMF was added slowly via syringe under nitrogen. Reaction mixture was stirred for 2 hours and then diluted with 25 ml of water. The pH of the solution was adjusted to 7.0 with 0.1N NaOH and then carefully concentrated under vacuum. The residue was suspended in methanol and the insoluble salts removed by centrifugation. The methanolic solution was concentrated to give 49 mg of crude product. This material was redissolved in water (25 ml) and added to a HP-20 column (40 ml of resin). The column was then eluted with various methanol-water mixtures (0%, 30%, 50%, 75% methanol). The fractions were analyzed by HPLC [Whatman ODS-3 RP-18 column, 50% acetonitrile/0.005M tetra-n-butylammonium phosphate buffer (pH 7.0), 44° C., 2 ml/minute, retention time=13 minutes] and the appropriate fractions combined and concentrated to give 34.1 mg of sodium 5-O-sulfate-13-deoxy-22,23-dihydroavermectin B₁ aglycon. The ¹H NMR spectrum (CD₃OD) of this product exhibited the characteristic downfield shift of the C₅-hydrogen to δ5.05 from δ4.28. The product also exhibited mass spectral and UV data consistent with its structure.

What is claimed is:

1. A compound having the formula:

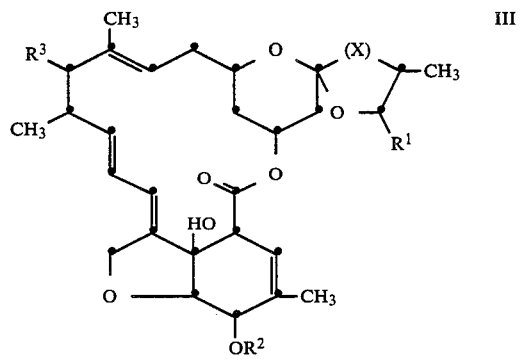

wherein:
X is

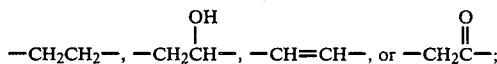

$R^1$ is methyl, ethyl, isopropyl, or sec-butyl;
$R^2$ is hydrogen, methyl, or —SO₃⊖M⊕ wherein M is a member selected from the Group I elements Li, Na, K, Rb, Cs and Fr, the Group II Be, Mg, Ca, Sr, Ba and Ra elements or an ammonium, diloweralkyl ammonium, or pyridinium cation;

$R^3$ is hydrogen, hydroxy, $-OSO_3^{\ominus}M^{\oplus}$, α-L-oleandrosyloxy, 4'-(O)—$SO_3^{\ominus}M^{\oplus}$-(α-L-oleandrosyloxy), 4'-(α-L-oleandrosyl-α-L-oleandrosyloxy, 4''-(O)—$SO_3^{\ominus}M^{\oplus}$-4'-(α-L-oleandrosyl)-α-L-oleandrosyloxy, wherein M is as defined above; provided that one of said $R^2$ or $R^3$ groups contains said $-SO_3^{\ominus}M^{\oplus}$ or $-OSO_3^{\ominus}M^{\oplus}$ substituents; and, physiologically acceptable salts thereof.

2. A compound of claim 1 which is a member of the group:

sodium 4''-O-sulfate-avermectin B1a;
sodium 4''-O-sulfate-avermectin B1b
sodium 4''-O-sulfate-22,23-dihydroauermectin B1a;
sodium 4''-O-sulfate--22,23-dihydroavermectin B1b;
sodium 4'',5-di-O-sulfate-22,23-dihydroavermectin B1a;
sodium 4'',5-di-O-sulfate-22,23-dihydroavermectin B1b;
sodium 4'',5-di-O-sulfate avermectin B1a;
sodium 4''-5-di-O-sulfate avermectin B1b;
sodium 4'-O-sulfate-22,23-dihydroavermectin B1b monosaccharide;
sodium 4'-O-sulfate-22,23-dihydroavermectin B1b monosaccharide;
sodium 4'-O-sulfate-avermectin B1a[/b] monosaccharide;
sodium 4'-O-sulfate avermectin B1b monosaccharide;
sodium 5-O-sulfate-13-deoxy-22,23-dihydroavermectin B1a aglycon;
sodium-5-O-sulfate-13-deoxy-22,23-dihydroavermectin B1b aglycon;
sodium 4''-O-sulfate-avermectin A1a;
sodium 4''-O-sulfate avermectin A1b;
sodium 4''-O-sulfate-avermectin B2a; and
sodium 4''-O-sulfate-avermectin B2b.

3. A method for the treatment of parasitic infections which comprises administering to an animal infected with parasites an effective amount of a compound of claim 1.

4. A composition useful for treating animals infected with parasites which comprises an inert carrier and an effective amount of a compound of claim 1.

5. A method for treating agricultural plants which comprises contacting plants exposed to pests and parasites with an effective amount of a compound of claim 1.

6. A pharmaceutical composition useful for treating agricultural plants exposed to pests and parasites which comprises an inert carrier and an effective amount of a compound of claim 1.

* * * * *